US010119901B2

(12) United States Patent
Casas

(10) Patent No.: US 10,119,901 B2
(45) Date of Patent: Nov. 6, 2018

(54) GEOLOGICAL SCANNER

(71) Applicant: MIKROSCAN TECHNOLOGIES, INC., Carlsbad, CA (US)

(72) Inventor: Victor Casas, Carlsbad, CA (US)

(73) Assignee: MIKROSCAN TECHNOLOGIES, INC., Carlsbad, CA (US)

( * ) Notice: Subject to any disclaimer, the term of this patent is extended or adjusted under 35 U.S.C. 154(b) by 0 days.

(21) Appl. No.: 15/036,501

(22) PCT Filed: Nov. 14, 2014

(86) PCT No.: PCT/US2014/065806
§ 371 (c)(1),
(2) Date: May 13, 2016

(87) PCT Pub. No.: WO2015/073897
PCT Pub. Date: May 21, 2015

(65) Prior Publication Data
US 2016/0299057 A1 Oct. 13, 2016

Related U.S. Application Data

(60) Provisional application No. 61/905,036, filed on Nov. 15, 2013.

(51) Int. Cl.
*G01N 21/21* (2006.01)
*H04N 1/21* (2006.01)
(Continued)

(52) U.S. Cl.
CPC ............. *G01N 21/21* (2013.01); *G01N 33/24* (2013.01); *G02B 21/0016* (2013.01);
(Continued)

(58) Field of Classification Search
CPC ............ G01J 4/00; G01N 21/21; G01N 33/24
See application file for complete search history.

(56) References Cited

U.S. PATENT DOCUMENTS 4,700,298 A 10/1987 Palcic et al.
5,018,029 A 5/1991 Ekhoff et al.
(Continued)

FOREIGN PATENT DOCUMENTS

CN 101430272 A 5/2009
CN 102035834 B 6/2013
(Continued)

OTHER PUBLICATIONS

Battmann et al. Telemedicine: Application of Telephathology-Remote miscroscopy for intraoperative diagnoses on frozen sections. Telemedicine pp. 1127-1130 (2000).
(Continued)

*Primary Examiner* — Roy M Punnoose
(74) *Attorney, Agent, or Firm* — Wilson, Sonsini, Goodrich & Rosati

(57) ABSTRACT

Disclosed are methods and apparatus for acquiring and displaying whole slide images of crystalline samples. In some embodiments, a slide is placed upon an imaging device with a motorized stage, and a digital imaging device, and all parts of the specimen are imaged and reassembled to display the entire slide as a single image, displayable on PC and transmittable across local and wide area networks and the Internet, then facilitating the acquisition multiple whole slide images of the slide under crossed polarizers rotated at different angles, with each image displayed to the viewer at the angle of polarization.

18 Claims, 5 Drawing Sheets

(51) Int. Cl.
*G02B 21/00* (2006.01)
*G02B 21/12* (2006.01)
*G02B 27/28* (2006.01)
*G01N 33/24* (2006.01)
*G02B 21/36* (2006.01)

(52) U.S. Cl.
CPC ....... *G02B 21/0092* (2013.01); *G02B 21/125* (2013.01); *G02B 21/367* (2013.01); *G02B 27/283* (2013.01); *H04N 1/2191* (2013.01)

(56) References Cited

U.S. PATENT DOCUMENTS

| | | | |
|---|---|---|---|
| 5,216,500 A | 6/1993 | Krummey et al. | |
| 5,216,596 A | 6/1993 | Weinstein | |
| 5,297,034 A | 3/1994 | Weinstein | |
| 5,333,052 A * | 7/1994 | Finarov | G01B 11/0641 356/369 |
| 5,432,871 A * | 7/1995 | Novik | H04N 1/32771 348/14.13 |
| 5,450,201 A * | 9/1995 | Katzir | G01N 21/8806 356/369 |
| 5,828,500 A * | 10/1998 | Kida | G01M 11/02 356/237.1 |
| 6,020,966 A * | 2/2000 | Ausschnitt | G01B 11/028 356/237.1 |
| 6,101,265 A | 8/2000 | Bacus et al. | |
| 6,208,374 B1 | 3/2001 | Clinch | |
| 6,272,235 B1 | 8/2001 | Bacus et al. | |
| 6,400,395 B1 * | 6/2002 | Hoover | G02B 21/24 348/80 |
| 6,452,625 B1 | 9/2002 | Kapitza | |
| 6,606,413 B1 | 8/2003 | Zeineh | |
| 6,674,881 B2 | 1/2004 | Bacus et al. | |
| 6,711,283 B1 | 3/2004 | Soenksen | |
| 6,847,729 B1 * | 1/2005 | Clinch | G02B 21/365 348/E7.087 |
| 6,905,300 B1 | 6/2005 | Russum | |
| 7,028,075 B2 | 4/2006 | Morris | |
| 7,035,478 B2 | 4/2006 | Crandall et al. | |
| 7,116,437 B2 | 10/2006 | Weinstein et al. | |
| 7,116,440 B2 | 10/2006 | Eichhorn et al. | |
| 7,149,332 B2 | 12/2006 | Bacus et al. | |
| 7,215,467 B2 | 5/2007 | Nakagawa | |
| 7,224,839 B2 | 5/2007 | Zeineh | |
| 7,257,268 B2 | 8/2007 | Eichhorn et al. | |
| 7,292,251 B1 * | 11/2007 | Gu | G02B 21/367 345/555 |
| 7,319,540 B2 | 1/2008 | Tipirneni | |
| 7,391,894 B2 | 6/2008 | Zeineh | |
| 7,432,486 B2 | 10/2008 | Tanemura et al. | |
| 7,502,519 B2 | 3/2009 | Eichhorn et al. | |
| 7,518,652 B2 | 4/2009 | Olson et al. | |
| 7,542,596 B2 | 6/2009 | Bacus et al. | |
| 7,602,524 B2 | 10/2009 | Eichhorn et al. | |
| 7,646,495 B2 | 1/2010 | Olson et al. | |
| 7,668,362 B2 | 2/2010 | Olson et al. | |
| 7,738,688 B2 | 6/2010 | Eichhorn et al. | |
| 7,755,841 B2 | 7/2010 | Christenson et al. | |
| 7,801,352 B2 | 9/2010 | Uchiyama et al. | |
| 7,826,649 B2 | 11/2010 | Crandall et al. | |
| 7,844,125 B2 | 11/2010 | Eichhorn et al. | |
| 7,856,131 B2 | 12/2010 | Bacus et al. | |
| 7,893,988 B2 | 2/2011 | Olson et al. | |
| RE42,220 E * | 3/2011 | Clinch | G02B 21/365 382/128 |
| 7,916,916 B2 | 3/2011 | Zeineh | |
| 7,941,275 B2 | 5/2011 | Gholap et al. | |
| 7,949,168 B2 | 5/2011 | Crandall et al. | |
| 7,979,212 B2 | 7/2011 | Gholap et al. | |
| 8,010,555 B2 | 8/2011 | Eichhorn | |
| 8,023,714 B2 | 9/2011 | Soenksen | |
| 8,086,077 B2 | 12/2011 | Eichhorn | |
| 8,094,902 B2 | 1/2012 | Crandall et al. | |
| 8,103,082 B2 | 1/2012 | Olson et al. | |
| 8,126,250 B2 * | 2/2012 | Cooke | G02B 21/367 382/133 |
| 8,189,897 B2 | 5/2012 | Leidenbach | |
| 8,200,767 B2 * | 6/2012 | Ariga | G02B 21/367 709/206 |
| 8,325,150 B1 | 12/2012 | Reeves et al. | |
| 8,456,522 B2 | 6/2013 | Olson et al. | |
| 8,515,683 B2 | 8/2013 | Gholap et al. | |
| 8,781,261 B2 | 7/2014 | Eichhorn | |
| 8,805,791 B2 | 8/2014 | Eichhorn | |
| 8,996,570 B2 | 3/2015 | Stratman et al. | |
| 9,230,153 B2 | 1/2016 | Casas | |
| 2002/0061127 A1 | 5/2002 | Bacus et al. | |
| 2002/0091548 A1 | 7/2002 | Auer et al. | |
| 2003/0123717 A1 | 7/2003 | Bacus et al. | |
| 2004/0066960 A1 | 4/2004 | McLaren et al. | |
| 2004/0085443 A1 | 5/2004 | Kallioniemi et al. | |
| 2004/0136582 A1 | 7/2004 | Bacus et al. | |
| 2005/0134687 A1 | 6/2005 | Kaminsky et al. | |
| 2006/0023201 A1 | 2/2006 | Malekafzali | |
| 2006/0104499 A1 | 5/2006 | Zahniser et al. | |
| 2006/0159367 A1 | 7/2006 | Zeineh et al. | |
| 2007/0103739 A1 | 5/2007 | Anderson, Jr. et al. | |
| 2007/0279735 A1 | 12/2007 | Sieckmann | |
| 2009/0028414 A1 | 1/2009 | Crandall et al. | |
| 2009/0076368 A1 | 3/2009 | Balas | |
| 2009/0098534 A1 | 4/2009 | Weier et al. | |
| 2009/0238435 A1 | 9/2009 | Shields | |
| 2009/0272186 A1 * | 11/2009 | Hall | G01N 1/2813 73/152.04 |
| 2010/0020299 A1 | 1/2010 | Zebala | |
| 2010/0067759 A1 | 3/2010 | Zeineh | |
| 2010/0103253 A1 | 4/2010 | Sieckmann et al. | |
| 2010/0194681 A1 | 8/2010 | Halushka | |
| 2010/0315502 A1 | 12/2010 | Tafas et al. | |
| 2011/0048142 A1 | 3/2011 | Pfeifer | |
| 2011/0090327 A1 | 4/2011 | Kenny et al. | |
| 2011/0217238 A1 | 9/2011 | Borrebaeck et al. | |
| 2011/0311123 A1 | 12/2011 | Gholap et al. | |
| 2012/0011151 A1 | 1/2012 | Eichhorn | |
| 2012/0038979 A1 | 2/2012 | Hing et al. | |
| 2012/0072452 A1 | 3/2012 | Stratman et al. | |
| 2012/0099769 A1 | 4/2012 | Eichhorn | |
| 2013/0182922 A1 | 7/2013 | Kil | |
| 2013/0265576 A1 * | 10/2013 | Acher | G01J 4/00 356/369 |
| 2014/0098209 A1 | 4/2014 | Neff | |
| 2014/0193839 A1 | 7/2014 | Cunningham | |
| 2015/0374276 A1 * | 12/2015 | Farkas | A61B 5/444 600/407 |
| 2015/0379328 A1 | 12/2015 | Casas | |
| 2016/0004902 A1 | 1/2016 | Casas | |
| 2016/0116729 A1 | 4/2016 | Casas et al. | |

FOREIGN PATENT DOCUMENTS

| | | |
|---|---|---|
| WO | WO-9930264 A1 | 6/1999 |
| WO | WO-02073246 A2 | 9/2002 |
| WO | WO-2008028944 A1 | 3/2008 |
| WO | WO-2013013117 A1 | 1/2013 |
| WO | WO-2015073897 A2 | 5/2015 |
| WO | WO-2016069794 A1 | 5/2016 |
| WO | WO-2017066635 A1 | 4/2017 |

OTHER PUBLICATIONS

Parvin et al. DeepView: A Channel for Distributed Microscopy and Informatics. Supercomputing, ACM/IEEE 1999 Conference, Nov. 13-18, 1999 (15 pgs.).
PCT/US2012/047527 International Preliminary Report on Patentability dated Jan. 21, 2014.
PCT/US2012/047527 International Search Report dated Oct. 1, 2012.
PCT/US2014/065806 International Preliminary Report on Patentability dated May 26, 2016.

(56) References Cited

OTHER PUBLICATIONS

PCT/US2014/065806 International Search Report and Written Opinion dated Feb. 19, 2015.
PCT/US2015/057890 International Search Report and Written Opinion dated Feb. 5, 2016.
U.S. Appl. No. 14/234,013 offfice Action dated Jan. 30, 2015.
U.S. Appl. No. 14/848,235 Office Action dated Oct. 29, 2015.
U.S. Appl. No. 14/853,763 Office Action dated Dec. 3, 2015.
U.S. Appl. No. 14/853,763 Office Action dated May 16, 2016.
PCT/US2015/057890 International Preliminary Report on Patentability dated May 11, 2017.
U.S. Appl. No. 14/848,235 Office Action dated Mar. 21, 2017.
U.S. Appl. No. 15/351,889 Office Action dated Mar. 24, 2017.
Co-pending U.S. Appl. No. 15/294,541, filed Oct. 14, 2016.
U.S. Appl. No. 14/848,235 Office Action dated Aug. 9, 2016.
U.S. Appl. No. 14/848,235 Office Action dated Nov. 3, 2016.
Co-pending U.S. Appl. No. 15/351,889, filed Nov. 15, 2016.
PCT/US2016/057137 Invitation to Pay Additional Fees dated Dec. 27, 2016.
PCT/US2016/057137 International Search Report and Written Opinion dated Mar. 3, 2017.
Fueten. A computer-controlled rotating polarizer stage for the petrographic microscope. Computers & Geosciences 23(2):203-208 (1997).
U.S. Appl. No. 14/848,235 Office Action dated Jun. 30, 2017.

\* cited by examiner

Mirror Blocks for Reflected Light Microscopy

A. Reflected Brightfield Configuration

B. Reflected Darkfield Configuration

C. Reflected Polarized Light Configuration

GEOLOGICAL SCANNER

CROSS REFERENCE

This application claims the benefit of U.S. Provisional Patent Application No. 61/905,036, filed Nov. 15, 2013, which is herein incorporated by reference in its entirety.

FIELD OF THE INVENTION

The following relates to material science and engineering, petrography, geological microscopy, material structure scanning, including industrial materials, microscopy training, geology education, research, and microscopy of crystalline structures.

BACKGROUND OF THE INVENTION

A microscope for studying materials (e.g., petrography) is a type of optical microscope used in material science, petrology and optical mineralogy to identify materials, rocks and minerals in thin sections. The microscope is used in material sciences, material engineering, optical mineralogy, and petrography. The method is called polarized light microscopy (PLM).

SUMMARY OF THE INVENTION

Disclosed herein are methods and apparatus for acquiring and displaying whole or partial images of materials, including but not limited to geological samples or specimens, rocks, minerals, metals, finished materials, industrial samples, parts and components with an opaque yet reflective nature, metals embedded into a medium and polished or ground for viewing and documentation, and/or crystalline samples or specimens. In some embodiments, a substrate or slide is placed upon an imaging device with a motorized stage, and a digital imaging device (e.g., camera or line scanner), and all parts of the specimen are imaged and reassembled to display the entire substrate or slide as a single image, displayable on a monitor and transmittable across local and wide area networks and the Internet. The displayed image is used for facilitating the acquisition of multiple whole slide or substrate images of the slide or substrate under crossed polarizers rotated at different angles, with each image displayed to the viewer at the angle of polarization.

In one embodiment, methods are disclosed of visualizing a specimen, the methods comprising the steps of: a) placing a specimen on a substrate, the specimen occupying an area of the substrate; b) placing the substrate on a stage and imaging the area of the substrate with the specimen using a high power magnification objective lens and crossed polarizer to obtain a single scan of the specimen at high magnification and high resolution, wherein the crossed polarizer is set in a single direction to provide data for a high resolution image of the specimen; c) repeating the imaging process of step (b) with the angle of the crossed polarizer changed at various angled increments, further comprising obtaining a continuous sequence of successive images by advancing a field of view of the high power objective lens of the microscope stepwise across the specimen and acquiring successive images of each field of view for the specimen, once at each angle of polarization; and d) uploading and storing the high resolution image data in a database for remote viewing.

In other embodiments, microscopy devices are disclosed comprising a device provided with at least one objective lens, a motorized turret, a digital imaging system and a motorized stage, a polarizer and an analyzer, the polarizer and analyzer forming a crossed polarizer capable of rotating about an axis, wherein the microscopy apparatus is controllable to obtain, a single scan of a specimen at a high magnification and high resolution to provide high resolution digital image data of the specimen occupying an area of a substrate placed upon the motorized stage, comprising a continuous sequence of successive images by advancing the field of view of a high power objective lens stepwise across the specimen thereby acquiring successive images of the entire field of view for the specimen, and taking successive scans at different angles of polarization; image processing means to process the high resolution digital image data to obtain a low resolution copy of the image data; a storage means to store the high resolution image data and the low resolution copy of the image data thereby obtained; a means for transferring the low resolution copy of the image data from the data store to the remote terminal for displaying a corresponding low resolution image, as a navigation map, upon a monitor of the terminal; and a means for transferring corresponding high resolution image data for the selected area of the image of the navigation map from the data store to the terminal.

In various aspects, provided herein is a scanner capable of acquiring one or more images of a specimen. Specimens include samples which are not usually processed for traditional microscopy viewing on slides. The term "specimens" or "samples" may be used interchangeably in the various embodiments disclosed herein. Examples of such specimens include, without limitation, rocks of various sizes, metal based samples, and samples, e.g., opaque samples, which require differential illumination over traditional microscopy where light cannot be delivered through the specimen. The specimens may be whole, cross-sections or any portion of a whole specimen. In many implementations, a specimen is scanned without destruction of the specimen, allowing a user to replace the specimen to the location from which it was derived. A scanner may be portable, wherein a specimen is scanned at the sampling location or a remote location. In some embodiments, a scanner comprises an illuminator with light source for illuminating a specimen, wherein the light is then reflected off of the specimen and onto an imaging device. In one embodiment, the imaging device, such as a camera, is a component of the scanner.

In one aspect, provided herein is an illuminator which provides coaxial illumination through an illumination light path (light path from a light source to a specimen) to a semi-silvered mirror (50% reflection beamsplitter) which is placed at a 45 degree angle from a primary objective path to the illumination path, allowing 50% of the light to be directed through an objective lens. The objective lens functions as a condensing lens of the same numerical aperture as the light collecting power of the same objective. In some embodiments, crossed polarizing filters are placed in the illumination light path to allow for polarized reflected light.

In one aspect, provided herein is an imaging device. In one embodiment, light reflected off of a specimen is collected, for example, through an objective lens, by an imaging device. Exemplary imaging devices include, without limitation, CCD, CMOS, line scan camera or line scanner, and other image sensing devices.

In one aspect, provided herein is a platform for holding one or more specimens. In one embodiment, the platform is a stage. The stage, in various implementations comprises a motorized stage. A motorized stage allows for a specimen to be moved relative to an illuminator (light source) and/or imaging device of a scanner. In another aspect, the platform is a mat. A mat, in certain circumstances, serves as both a platform and as a display. For example, a specimen is placed on the mat and an image of the specimen is acquired using a scanner. The specimen may subsequently be removed from the mat, and the acquired image is then displayed on the mat. In another or additional embodiment, the mat functions as a touchpad. A touchpad is useful for annotating an acquired image. A touchpad may also include a control panel, whereby subsequent specimen acquisition image details, e.g., resolution, selection of specimen area for imaging, are controlled. In some embodiments, the macro image using the mat is used for determining the scan area at higher magnification of a large sample.

In another aspect, provided herein are one or more displays for viewing one or more acquired images. In an exemplary embodiment, a display allows a user to view image data from a specimen as well as corresponding information regarding the specimen. Specimen information includes analysis of one or more images of the specimen. Specimen information may further include mineral content of the specimen. In other or additional aspects, information regarding the specimen includes coordinates for identifying the location from which a specimen was acquired. In an exemplary embodiment, a display is a geomap. A geomap is an interactive map which allows a user to view specimen images and corresponding data (e.g., specimen analysis such as mineral content) along with specimen coordinates. The geomap, in various embodiments, comprises specimen images and corresponding data from a plurality of user provided data.

In one embodiment, image data from a scanned specimen is stored with specimen coordinate data, which identifies the location of the retrieved specimen. The scanner may be a 2D or 3D scanner configured to obtain low resolution, high resolution, or both low and high resolution images of the specimen. In an exemplary embodiment, the scanner comprises polarizing filters.

In another aspect, provided herein are systems and methods for the acquisition of low, high or low and high resolution images using one or more scanners. In some embodiments, one scanner has polarizing means. Each scanner acquires one or more images of a sample and stores the images on a server or computer for display. In exemplary embodiments, a user of a scanner inputs global position system coordinates for inclusion with image data.

Further provided herein, in various embodiments, are methods of scanning a specimen. The methods may include the use of a scanner as described herein or other commercially available scanners. A scanner may capture one or more images of a specimen in two- or three-dimensions.

In one embodiment, a method for scanning a specimen comprises placing a specimen on a platform such as a stage or mat. The stage or mat may be movable by manual or electronic means. A scanner acquires one or more images of the entire specimen, or an area of interest of the specimen. If more than one image is acquired, the images are reassembled for display as a single image. Data for the acquired images and reassembled images are transmittable across local and wide area networks and/or the Internet for display at any location. In some embodiments, the viewed images are annotated. In other or additional embodiments, the viewed images are used as guide to control the subsequent acquisition of additional images of the specimen, for example, high resolution images. In other or additional embodiments, a user interacts with a display using software to acquire additional images of the specimen and/or to annotate and/or analyze the specimen. The display may facilitate the acquisition of multiple images of the specimen under crossed polarizers rotated at different angles, with each image displayed at the angle of polarization. In certain embodiments, multiple z-planes are acquired and reassembled to provide an extended depth of field image. In one embodiment, one or more images of a specimen are acquired using a two-dimensional scanner without polarizing means. In this embodiment, the images are viewed on a display and used as a template for a user to subsequently scan the specimen using a polarized scanner.

DETAILED DESCRIPTION OF THE INVENTION

Figure 1:
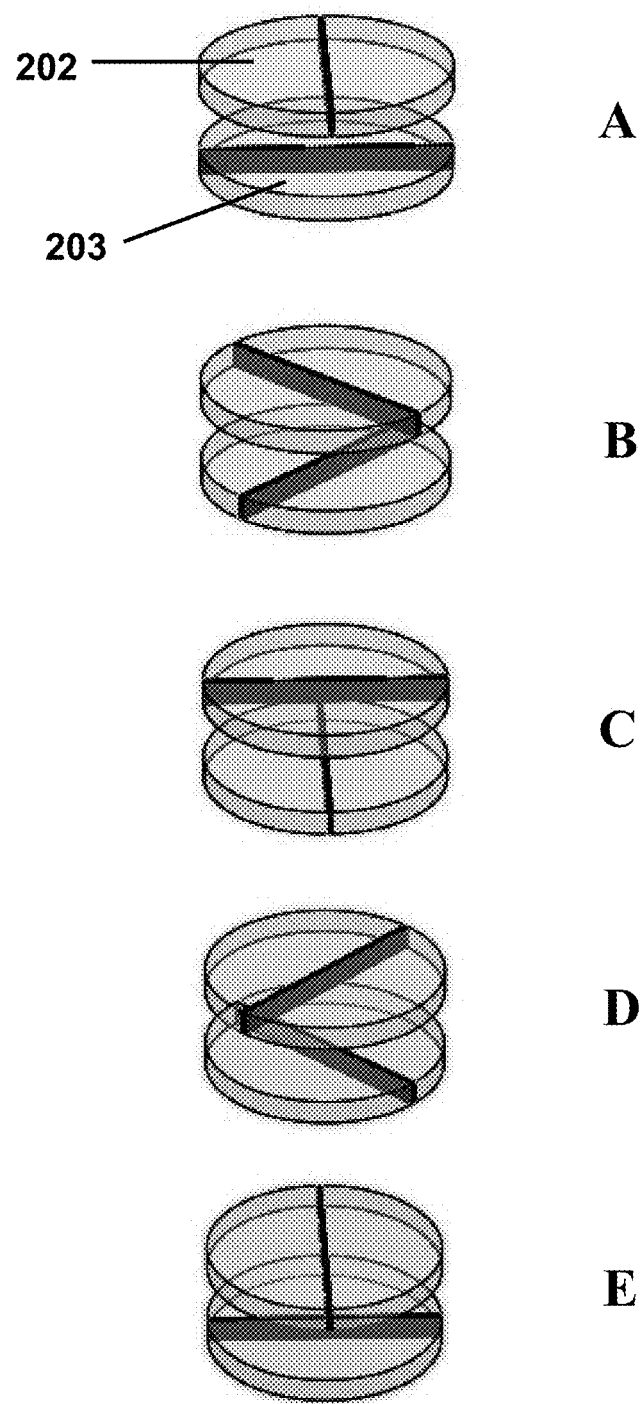
FIG. 1 depicts a non-limiting exemplary embodiment of a geologic scanner, wherein two polarizers (polarizer and an analyzer) are crossed relative to each other. In this embodiment, the polarizers are rotated in synchrony in 45 degree increments. Further in this embodiment, an image is captured at each of five increments of rotation. Not depicted in FIG. 1 is the stage and sample that is normally positioned between the two polarizers.

Digital pathology, or the digitizing of entire slides of biological tissue, has been used and shown to be a useful method of storing and sharing microscope slides across great distances or cataloguing libraries of tissues, diseases, etc. Because of technical hurdles, such as the need to rotate slides and the inability to tile rectangular images across a slanted image, this technique has not been extended to include industrial, petrographic, geological, metallic or crystalline microscopy samples. Provided herein, in various aspects, are methods and systems for acquiring, storing, sharing, and/or analyzing images of such industrial, petrographic, geological, metallic and crystalline samples using a polarizing scanner. A polarization scanning device is useful for viewing samples comprising anisotropic material, where color is an important property useful for mineral identification. Thus the methods and systems provided herein allow for the acquisition of an image of a geological sample using a scanner with polarizing means, where the images may be digitally stored, viewed and/or analyzed for grain size and shape, crystallinity and/or morphology, which aids in the identification and analysis of the sample. In another embodiment, characteristics of a sample investigated using a polarizing scanner include, without limitation, pleochroism, refractive index, mineral content, birefringence, twinning, inclusions and cleavage characteristics. In addition to industrial, geological, petrographic, crystalline and metallic samples, additional materials may be scanned using the systems and methods provided herein including, but not limited to, natural and industrial minerals, cement composites, ceramics, metals, minerals, mineral fibers, rocks, polymers, starch, wood, biological samples having anisotropic materials, finished materials, industrial parts and components with an opaque yet reflective nature, metals embedded into a medium and polished or ground for viewing and documentation, crystalline samples and other samples having anisotropic materials.

Crystalline structures such as rock and crystals and many forms of acid require, to be viewed under a microscope, for that microscope to be fitted with two polarizing filters termed the polarizer and analyzer, and the specimen rotated at small increments to view the effect of polarized light upon the crystalline substances to identify and label them properly. In one aspect, the methods, systems and apparatus described herein provide two polarizing filters, a polarizer and an analyzer, as components of a microscope for use in digital microscopy. The microscope may comprise or be operably connected to, e.g., in a scanner, an imaging device for acquiring images of a specimen. The polarizer is positioned beneath a specimen stage with the polarizer vibration azimuth starting in the left-to-right, or East-West direction, although these elements are capable of being rotated through 360 degrees and may be motorized. The analyzer starts aligned with a vibration direction oriented North-South, but again capable of being rotated with, for example, a corresponding motor, is placed above the objectives of the microscope, wherein the analyzer and polarizer vibration azimuths are positioned at right angles to each other. In this configuration, the polarizer and analyzer are said to be crossed, with no light passing through the system and a dark view field present to the imaging device. When a specimen is placed into the system, the specimen is scanned by taking digitized images of each field comprising a substrate holding said specimen, such a substrate includes a microscope slide, and reassembling the images as a single image. The images may be uploaded and reassembled through a web based program, for example a program similar to Qumulus, optionally with described modifications.

The system then rotates the polarizer and analyzer 45 degrees at the same time, so that the polarizing filters are still crossed, and another scan is acquired. This may occur a total of 5 times so that each stop along a 180 degree arc of crossed polarization is covered.

Each assembled image is labeled with the name of the image plus a degree mark (for instance ABC0, ABC45, ABC90, ABC135, ABC180), and the image collected is saved and uploaded to a server.

In additional methods and systems described herein, two polarizing filters are positioned on the same side of a platform holding a specimen. The polarizing filters, polarizer and analyzer, are crossed in a beamsplitter cube disposed along both a path between a light source and the specimen (illumination path) and a path between the specimen and an imaging device (reflective path). The light source and imaging device, in many implementations, are components of a digital scanner. In an exemplary method, a specimen is placed on a platform and scanned. The scanner rotates the polarizer and analyzer 45 degrees at the same time, maintaining a crossed configuration, and an image is acquired using the imaging device each time the polarizers are rotated. The acquired images are then reassembled as a single image using software or a web based program such as Qumulus. Each assembled image is labeled as previously described, with an image name and a degree mark. Images are saved and optionally uploaded to a server.

The server, in many implementations, hosts a web viewer which displays the primary image (for example, ABC0) for viewing. Since the image consists of multiple tiled or scanned images, the image can be zoomed in and/or panned about, displaying a magnified view of the entire specimen and/or microscope slide, only processing that which is viewed at one time.

To optimize time and speed, the image can be displayed in the "Tiled Pyramidal Files" format, so that a full, high resolution image is viewed which contains all of the folders, however when backing off and obtaining lower magnification views, a new image of a lower resolution would be loaded in its place.

The viewer allows the person or user viewing the images to "rotate" the image, at 45 degree increments. When "rotated", the corresponding image loads with the precise field being viewed in place at an angle corresponding to the degrees at which the polarizer was rotated when the image was taken, at the same zoom factor as the current image is being viewed.

As an example, a user acquires five images of a specimen using a system described herein, and uploads the images. The user zooms in on an image so that the object or area the user is interested in takes up most of the screen of the viewer. The user then "rotates 45 degrees" and a new image loads with the same object, however it loads at a 45 degree angle from the original image. This way it feels to the user as though they are rotating the specimen, which is what they would be doing on a petrographic microscope.

Provided herein, in various embodiments, is a system for the acquisition and display of one or more images of a specimen. Specimens include, without limitation, industrial, petrographic, geological, metallic and crystalline samples. In an exemplary embodiment, the system comprises (a) a scanner, (b) an image acquisition system controlled by a user, (c) a server workflow and viewing system to display the images post-acquisition, and (d) a display for an end user to view the acquired images. In one embodiment, the scanner comprises a G2 scanner. In one embodiment, the acquisition system is a computer comprising software or a web based program to control the scanner for image acquisition. In one embodiment, the server resides at the specimen acquisition site. In another embodiment, the server resides at a location remote from the specimen acquisition site. In an additional or other embodiment, the server is a cloud based server, capable of residing at the acquisition site or in a remote datacenter. In one embodiment, the display is a device such as a computer, tablet, television (e.g., smart TV), smartphone or any network enabled device capable of viewing images.

In some embodiments, the imaging system/apparatus does not comprise a rotation of polarizers or analyzer in the beamsplitter cube on reflected specimens. In some embodiments, specimen rotation is not required or desired in reflected light.

Referring to FIG. 1, in a particular embodiment, a polarizing filter is positioned above the stage and sample and another polarizing filter is positioned below the stage and sample. In this embodiment, the two polarizing filters, the polarizer 202 and analyzer 203, are crossed relative to each other and rotated in synchrony in five 45 degree increments. Further in this embodiment, an image is captured at each of five increments of rotation (A-E). The images are optionally reassembled at a later time point to emulate rotation of the sample.

Figure 2:
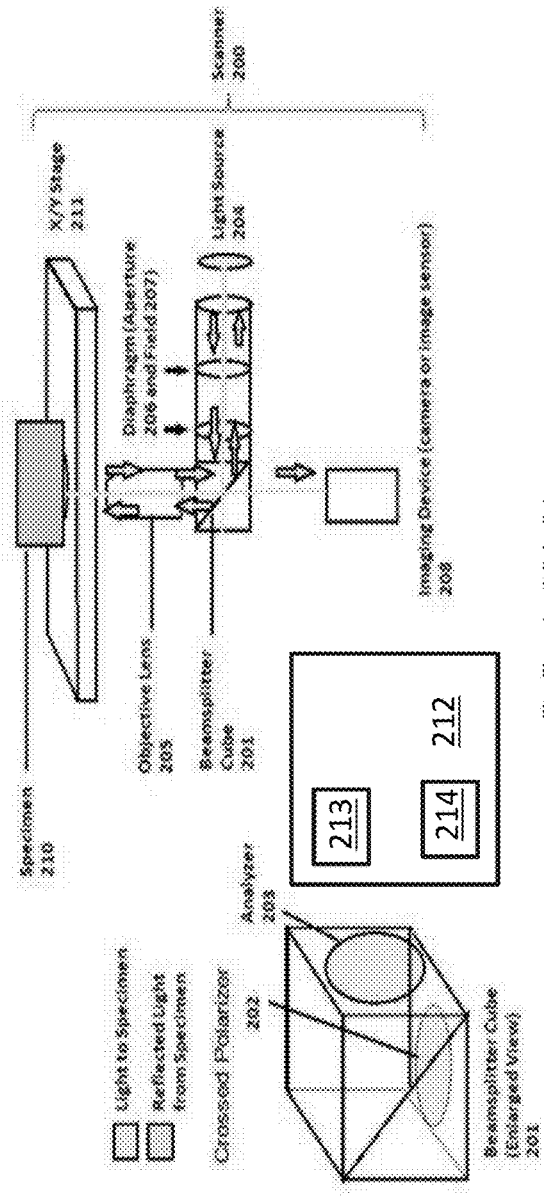
FIG. 2 depicts an exemplary scanner comprising a polarizing beam splitter cube.

In another aspect, provided herein is a system comprising two polarizing filters which are both located above or below a stage holding a specimen. The two polarizing filters are components of a scanner useful for acquiring images of the specimen. An exemplary scanner, 200, is shown in FIG. 2. The scanner includes a light source, 204, for illuminating a specimen, 210. In this figure, the illuminating light travels through a light path (illumination path) comprising a beamsplitter cube, 201, wherein the beamsplitter cube comprises two polarizing filters: a crossed polarizer, 202, and an analyzer, 203. The light path in this example further comprises a diaphragm (aperture, 206, and field, 207). The scanner of FIG. 2 is operably connected to, and/or comprises an imaging device, 208, for receiving and capturing light reflect off of the specimen. The reflected light travels from the specimen to the imaging device along a reflection path. In this figure, the reflection path comprises an objective lens, 205. The specimen in FIG. 2 is held by a stage, 211.

Scanner

In one aspect, provided herein is a scanner comprising a light source for illuminating a specimen. In some embodiments, the intensity of light directed to a specimen from the light source is adjustable. A light source includes, without limitation, a light-emitting diode (LED). LEDs include white light, red light, green light and blue light LED. In some instances, the system comprises a mirror which reflects light from an external source to a specimen to be scanned. In other embodiments, the light source is a cold cathode fluorescent lamp (CCFL). In many implementations, the light source is guided to the specimen via optical components disposed along a light path (illumination path) between the light source and the specimen. Optical components include mirrors, filters and lenses. In other or additional embodiments, the scanner comprises or is operably connected to an imaging device. The imaging device may comprise a CCD (charge-coupled device) imager, CMOS, line scanner or other imaging device.

In some embodiments, a light path between the scanner light source and the specimen or sample comprises a diaphragm. In one embodiment, a diaphragm is an aperture diaphragm. An aperture diaphragm is useful for inhibiting the passage of light, except for light which may pass through an aperture of the diaphragm, wherein the size of the aperture regulates the amount of light which may pass through the diaphragm. In one embodiment, a diaphragm is a field diaphragm.

In some embodiments, a light path between the scanner light source and the specimen comprises two polarizing filters, a polarizer and an analyzer. The polarizing filters may be located on one side of the specimen, for example, as in FIG. 2. In other embodiments, the specimen is located between the polarizing filters, for example, as in FIG. 1. In the case where the polarizing filters are located on the same side of the specimen, in many implementations, the polarizing filters are crossed in a polarizing cube beamsplitter. An exemplary beamsplitter cube having a polarizer and analyzer is shown in FIG. 2. A polarizer is an optical filter that passes light of a specific polarization while blocking light of other polarizations. In many implementations, the polarizer is useful for converting a beam of light of undefined or mixed polarization into defined polarized light. The polarizer may be a linear or circular polarizer. Linear polarizers include absorptive and beam-splitting polarizers. A second polarizing filter of a system can be generally referred to as an analyzer.

In some embodiments, a light path between the specimen and the imaging device (e.g., reflection or transmission path) comprises an objective lens. The objective lens, in many implementations, acquires light reflected and/or transmitted from the specimen and projects said light to the imaging device. In some implementations, the system comprises a plurality of objective lenses, wherein at least two of the plurality of objective lenses have different optical powers. For example, a system comprises a 4×, 10×, 40× or 100× objective lens, or a combination thereof. In some embodiments, a view of the specimen is focused by moving the objective lens relative to the specimen. In additional embodiments, a scanner comprises a lens changing device, wherein the lens changing device may be motorized. In some instances, the lens changing device is manually or automatically controlled with the use of a software program.

In some embodiments, an objective lens of the system is a high powered objective lens suitable to obtain a single scan of the entire specimen at high magnification and high resolution. In other or additional embodiments, the objective lens of the system is a low powered objective lens suitable to obtain a plurality of images of the entire specimen at low resolution, wherein the plurality of images may then be assembled into a single, low resolution image. In some embodiments, the imaging device acquires a continuous sequence of successive images by advancing a field of view of a high powered objective lens stepwise across the entire sample. In some instances, high resolution image data obtained is processed to generate data for a relatively low resolution copy of the images. In some embodiments, the high resolution image data and the low resolution copy of the image data is saved in a metadata file. In other embodiments, the imaging device optically captures low resolution data from a low magnification image of the sample.

In one aspect, provided herein is a scanner comprising an imaging device, wherein light emitted from the light source and reflected from and/or transmitted through the specimen, depending on the scanner type (e.g., polarized or non-polarized) and/or specimen (e.g., microscopy specimen or geological specimen), is directed to an imaging device. An imaging device transforms optical signals to corresponding electric signals to become digital signals recognizable by a computer. Digital signals are transferable to a computer by interfaces including, but not limited to, the Internet, enhanced parallel port (EPP), bluetooth, universal serial bus (USB) and small computer system interface (SCSI). In one aspect, an imaging device comprises a surface photoelectric device fabricated to perform photoelectric transformation, for example, a charge-coupled device (CCD). In alternative embodiments, the imaging device comprises a CMOS, line scan camera or other image sensing device.

In one aspect, provided herein is a system comprising a platform for holding a specimen for scanning In some embodiments, a platform is a stage. In one embodiment, the specimen is prepared on a substrate, such as slide, for placement on a stage. In one embodiment, the stage is movable, wherein the position of the stage, and thus the specimen, is controlled manually or automatically, optionally with the use of a software program. In other or additional embodiments, a platform is a mat. A mat is configured to hold specimens which are not traditionally prepared on a slide, for example, geological specimens.

Figure 3:
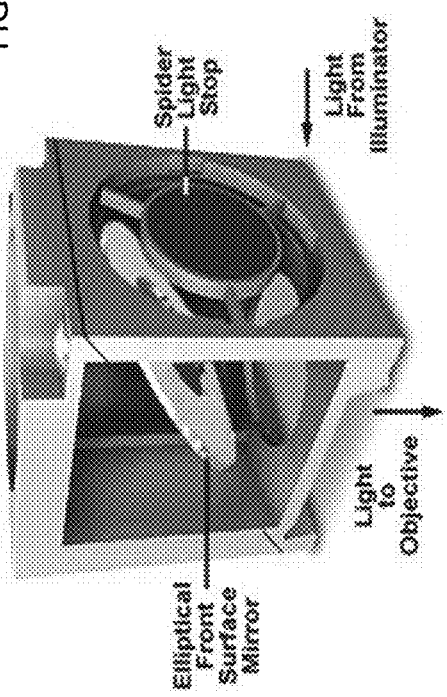
FIG. 3 depicts embodiments of darkfield mirror block in a reflected light system.

In some embodiments, the apparatus disclosed herein comprises a reflected light system, or use of the same;

referring to FIG. 3. The reflected light system disclosed herein allows a user to choose in advance an area, and/or to scan the entire area. In additional embodiments, the reflected light system is able to reassemble the images and upload them to a web based viewer hosted either on a local server or on a remote, cloud based server.

In some embodiments, a reflected light system is used which acquires and assembles images as a single image. In some applications, the reflected light system acquires and assembles images manually; the system operator moves the stage and adds each picture as he/she moves the stage, followed by saving the picture(s) in a single image format (e.g., a single bitmap rather than a pyramidal tiled file viewable via web browser).

In some embodiments, the system and apparatus disclosed herein comprises a darkfield illumination, or use of the same. In some implementations, the reflected darkfield illumination polarizing microscope comprises an opaque occluding disk placed in the path of the light traveling through the vertical illuminator so that only the peripheral rays of light reach the deflecting mirror. In certain applications, these rays are reflected by the mirror and pass through a hollow collar surrounding the objective to illuminate the specimen at oblique angles, including highly oblique angles. Light entering the mirror block is reflected by a special mirror positioned within a tube inside the block. This mirror is oriented at a 45-degree angle to the incident beam and has an elliptically shaped opening surrounded by a fully silvered front surface mirror. In some embodiments, peripheral rays of light reflected from the elliptical mirror are deflected downward, exiting at the bottom of the vertical illuminator. The cylinder of light then travels through the nosepiece before passing into customized darkfield objectives. These objectives are typically designed with optical corrections necessary for use on specimens lacking a cover slip.

Figure 4:
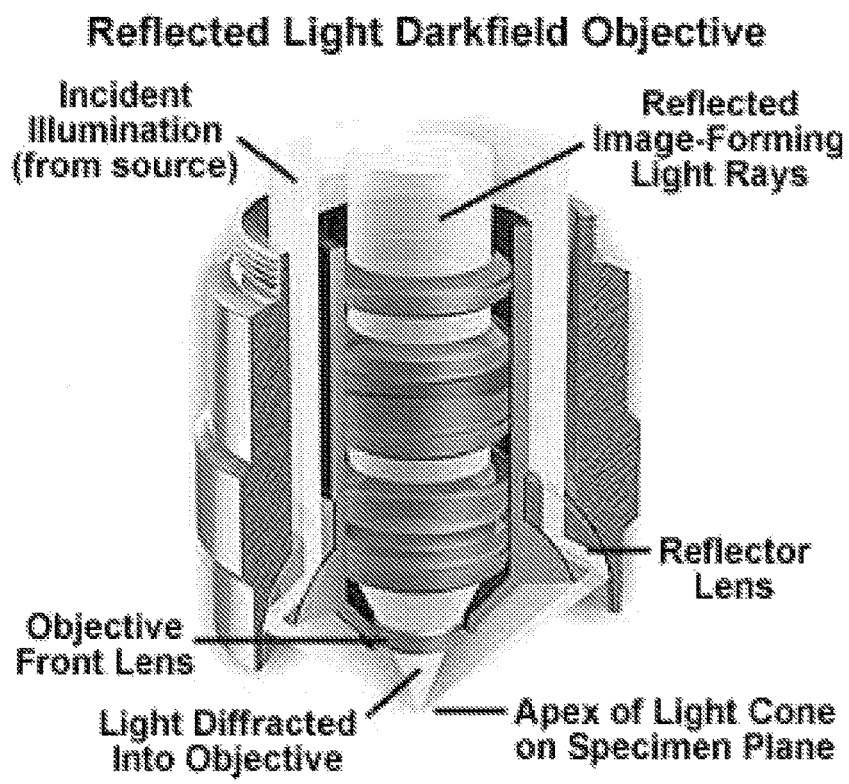
FIG. 4 depicts embodiments where light travels through darkfield mirror blocks.

In some embodiments, light from a darkfield mirror block travels down the 360-degree hollow chamber surrounding the centrally located lens elements of the specially constructed BD reflected light objectives, as illustrated in FIG. 4. This light is directed at the specimen from every azimuth in oblique rays to form a hollow cone of illumination by means of circular mirrors or prisms located at the bottom of the objective's hollow chamber. In this manner, the objective serves as two separate optical systems coupled coaxially such that the outer system functions as a darkfield "condenser" and the inner system as a typical objective. The image is then passed through the objective and tube lens, and collected on the CCD, CMOS, Line Scanner, or other imaging devices.

Figure 5:
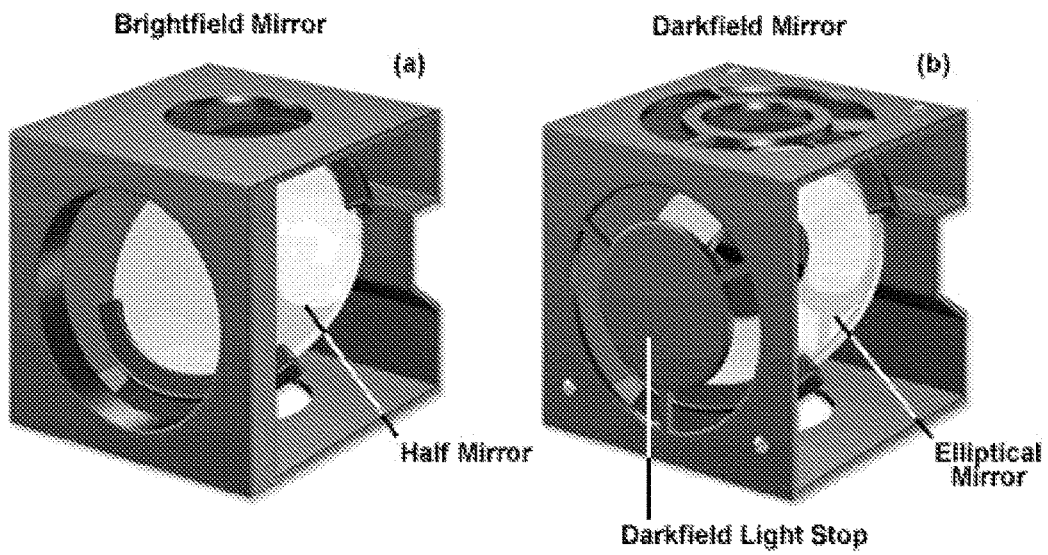
FIG. 5 depicts embodiments for mirror blocks in light reflected microscopy. A. Brightfield Mirror; B. Darkfield Mirror.

FIG. 5 presents embodiments where mirror blocks are used for reflected light microscopy. In the embodiments where brightfield mirror blocks are incorporated, a half mirror is used and a side of the cube is open. In other embodiments where a darkfield mirror is incorporated, an elliptical mirror is used, and a side of the cube is installed as a darkfield light stop.

Figure 6:
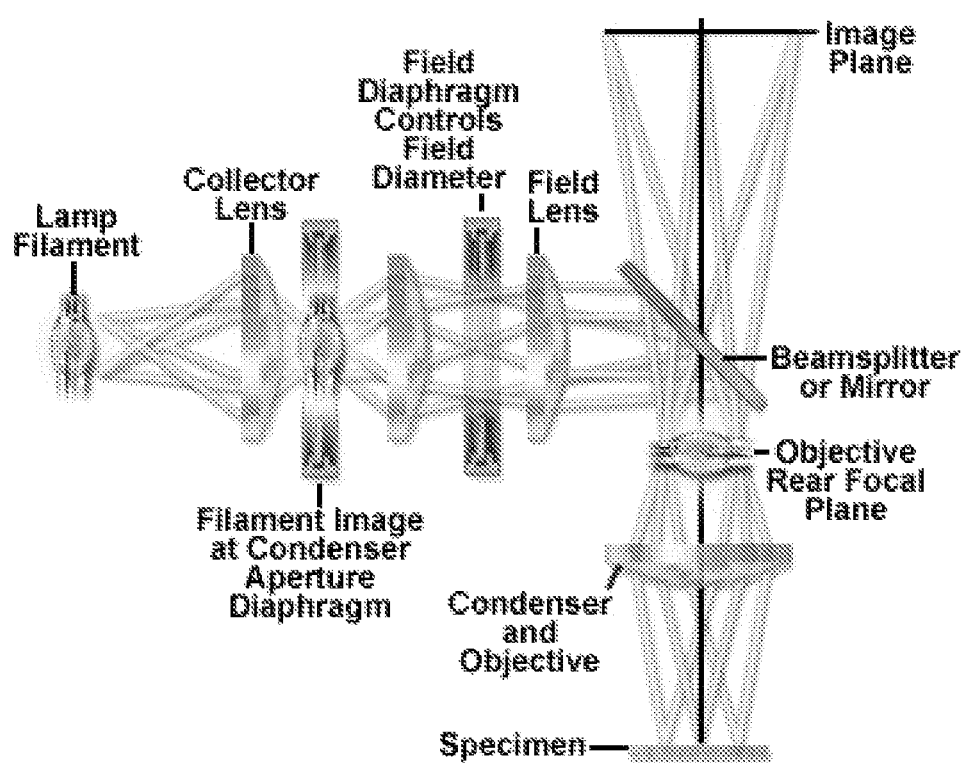
FIG. 6 depicts embodiments of imaging apparatus comprising a Kohler illumination in reflected light microscopy.

Referring to FIG. 6, in some embodiments, the imaging apparatus comprises a Kohler illumination system in reflected light microscopy. The Kohler illumination system comprises a lamp filament which generates light which passes through a collector lens, an aperture, and field lens. The beamsplitter deflects the light onto the specimen. The light reflected by the specimen is further passed through the beamsplitter and projected on an image plane.

Figure 7:
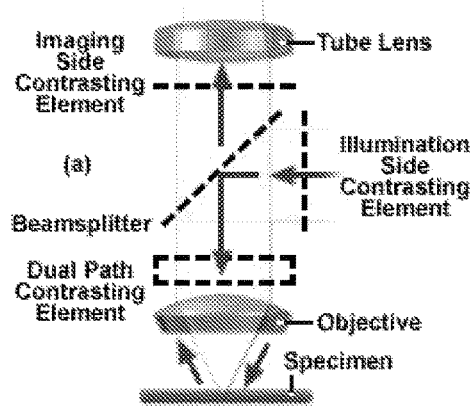
FIG. 7 depicts embodiments of contrast mechanisms in reflected light microscopy. A. Reflected Brighfield Configuration; B. Reflected Darkfield Configuration; C. Reflected Polarized Light Configuration.
Figure 7:
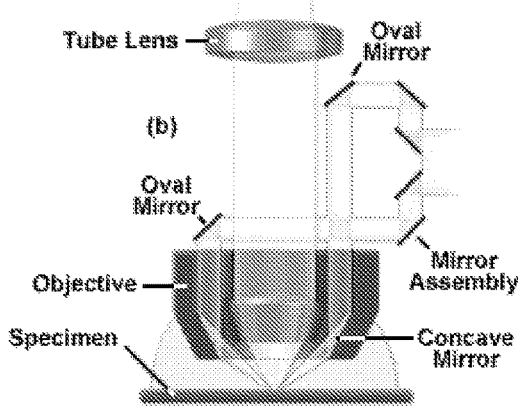
Figure 7:
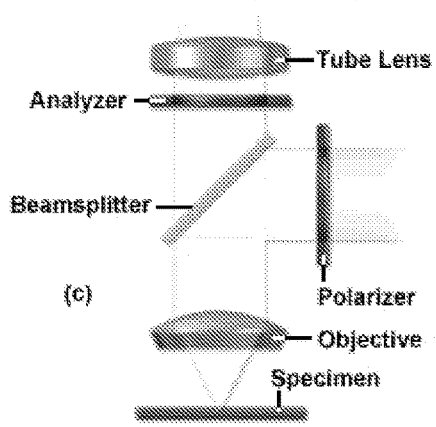

Referring to FIG. 7, the imaging apparatus in some implementations comprises contrast mechanisms in reflected light microscopy. In some embodiments of reflected brightfield configuration, the light from an illumination source is shed on a beamsplitter which directs the light onto the specimen. In some embodiments of reflected darkfield configuration, the light from an illumination source is passed by a sequence of mirrors (e.g., oval mirror, concave mirror) to the specimen; the reflected light from the specimen eventually reaches the tube lens and forms an image. In some embodiments of reflected polarized light configuration, the light from an illumination source travels through a polarizer and is deflected by the beamsplitter onto the specimen; the reflected light from the specimen then travels back through the objective, beamsplitter, analyzer, and tube lens.

Image Acquisition System and Server

Further provided herein is an image acquisition system or digital processing device for controlling the acquisition of an image of a specimen using a scanner. The image acquisition system may include a computer comprising software or a web based program for remote viewing of the image. Further provided herein is a server and viewing system for the display of acquired images.

Digital Processing Device

In some embodiments, the apparatuses, platforms, devices, systems, methods, media, and software described herein include a digital processing device 212, or use of the same. In further embodiments, the digital processing device 212 includes one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the descriptions disclosed herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

Non-Transitory Computer Readable Storage Medium

In some embodiments, the apparatuses, platforms, devices, systems, methods, media, and software disclosed herein include one or more non-transitory computer readable storage media 213 encoded with a program 214 including instructions executable by the operating system of an optionally networked digital processing device 212. In further embodiments, a computer readable storage medium is a tangible component of a digital processing device 212. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the apparatuses, platforms, devices, systems, methods, media, and software disclosed herein include at least one computer program 214, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB. NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB. NET, or combinations thereof. Compilation is often performed, at least in part, to create an executable program. In some embodiments, a computer program includes one or more executable complied applications.

Web Browser Plug-In

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the apparatuses, platforms, devices, systems, methods, media, and software disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the apparatuses, platforms, devices, systems, methods, media, and software disclosed herein include one or more databases, or use of the same. In view of the disclosure provided herein, those of skill in the art will recognize that many databases are suitable for storage and retrieval of mineralogical, petrographical and petrological images/information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Networking Modules

In some embodiments, the apparatuses, platforms, devices, systems, methods, media, and software described herein include one or more networking modules, or use of the same. In some embodiments, the network module is part of the apparatus/platform/system/device, or is coupled with the apparatus/platform/system/device. The network module is wired, or wireless, or a combination of wired and wireless. The wired module comprises one or more of the following: twisted electrical wires, telephony lines, printed electrical/electronic wires, coaxial cables, and optical fibers. The wireless module comprises a cellular interface, or a non-cellular interface, or a combination of cellular interface and non-cellular interface. In certain embodiments, the networking module operates on satellite communication and/or global positioning system (GPS). People with skills in the art can easily recognize various protocols running on the network; non-limiting examples include: the Internet protocol, TCP protocol, FTP, UDP, XML, and data binding scheme like XSD.

In some embodiments, the networking module is an electronic logic specifically designed for transmitting the data (e.g., material, structural, mineralogical, petrographical and/or petrological images/information). In some embodiments, the networking module is a portable digital processing device (e.g., smartphones, tablets, portable computers, laptops, desktops, all-in-one computers, palm computers, etc) coupled with the imaging apparatus/platform/system/device for data transmission.

End User Display

Further provided herein is an end user display for displaying acquired images. In many embodiments, the end user display provides information for the displayed acquired images. Information includes specimen coordinates and image annotations and/or analyses. Image analyses include specimen mineral content and descriptions of acquired images. Specimen coordinates are useful for generating a geomap. An end display, in various embodiments, is a geomap comprising specimen images and corresponding specimen information which are connected to the coordinates from where the specimen originated. An end display is viewable by a plurality of users. A display is any network enabled device capable of viewing images, including, but not limited to, a computer, tablet, smartphone and television.

Geographic Map

In some embodiments, the apparatuses, platforms, devices, systems, methods, media, and software described herein include one or more geographic maps, or use of the same. The geographic map is stored locally and/or remotely in a computing device (e.g., a server). In additional embodiments, the range of the geographic map covers one or more of the following: a building, a street, a town, a region, a site, a city, a state, a nation, and the globe. The map is associated with the mineralogical, petrographical and/or petrological images/information.

In certain embodiments, the geographic map comprises an interface with a user, wherein the user is a local user or/and a remote user. The user can click a location to obtain the mineralogical, petrographical and/or petrological images/information associated with the location.

Methods

In one aspect, provided herein is a method of acquiring an image of a specimen for further analysis and/or geotagging, comprising (a) obtaining a specimen from a given location, (b) optionally recording the coordinates of said location, wherein the coordinates are identified using a global positioning system, (c) positioning the specimen on a platform, wherein the platform is a stage or mat, (d) imaging an area of the specimen using an objective lens and crossed polarizer to obtain a single scan of the specimen, (e) repeating the imaging process of step (d) with the angle of the crossed polarizer changed at various increments one or more times to acquire successive images of each field of view of the specimen at each angle of polarization, and (e) storing the image data and optional coordinate data in a database. In one embodiment, the specimen is imaged using a high power magnification objective lens to obtain scans of the specimen at high resolution and high magnification. The high resolution image data is optionally processed to obtain a relatively low resolution copy of a composite image of the specimen. In an additional or other embodiment, the method further comprises optically capturing a low resolution and/or low magnification image of the specimen and storing said image data.

In another aspect, further provided herein is a method for acquiring images of a specimen using two or more scanners, wherein one scanner is a polarizing scanner. For example, a traditional scanner is used to scan one or more images of a sample provided to a system on a mat, wherein the images are two- or three-dimensional. A second scanner with polarizing filters are additionally utilized to obtain images of a specimen for metallurgical analysis. Image data from both scans are uploaded onto a server for viewing and further analysis. In one embodiment, a non-polarizing scan is completed and the resulting image is used as a template to guide a user to obtain additional images using a polarizing scanner.

In another aspect, further provided herein is a method of annotating an acquired image of a specimen using the platform of the system. As previously described, a specimen may be placed on a mat and scanned. In some embodiments, the scanned specimen is removed from the mat and the mat serves as a display for viewing the scanned image. In one embodiment, the image of the specimen on the map is an interactive image, which can be rotated and zoomed using the map as a control panel. The image may be analyzed for mineral or metallic content and annotated. The image may be annotated with specimen coordinate information.

In another aspect, provided herein is a method of controlling the acquisition of one or more images of a sample using one or more previously acquired images as a template. In an exemplary embodiment, an acquired image is stored to a network and viewed on a display. In one embodiment, a live display of the specimen is simultaneously viewed on a display. One or more images of the live specimen are acquired using the stored image as a guide. The live images may be high or low resolution and use any scanner described herein.

Specimens and Samples

The imaging apparatus disclosed herein includes specimens and/or samples, or use of the same. Non-limiting examples suitable for any kinds of imaging apparatuses include industrial, petrographic, geological, metallic or crystalline microscopy samples, including geological rocks, stones, sands, solid objects, minerals, natural composites, and/or compounds. In some embodiments, non-limiting examples include non-geological metals, parts, components, composites, etc that are opaque and have a reflective nature but are not necessarily geological by nature. In various embodiments, non-limiting examples include industrial objects, any human-made objects, such as industry devices, semiconductors, conductors, insulators, plastic, nonplastic, aerospace, and/or manufacturing.

EXAMPLES

Example 1

Geological Scanner and Method of Use

An area of geological interest is identified for petrographic analysis. The area comprises a variety of specimens for which mineral analysis is to be performed. A specimen is obtained from the area of interest, and a macro image of the specimen is taken with a mobile device. The coordinates of the obtained specimen are saved along with the macro picture and uploaded to the server, or are manually placed upon the specimen via a label. The coordinates are labeled on either the surface of the specimen, which may be viewed on acquired images of the specimen at a later date, or the coordinates are digitally recorded to a database. If the specimens are labeled without a macro photograph taken, then the specimen is placed on a platform or mat of a macro scanning system. A macro image is then taken of the sample, and the user selects the area of the specimen to be scanned from the macro image, and that area then serves as the "map" of the image. The high magnification scanning system comprises a digital polarizing scanner having at least the following optical components: a polarizing beam splitting cube comprising crossed polarizer and analyzer, an LED light source, a CCD camera and an objective lens. The LED light is directed along an illumination light path having the beamsplitter cube to the platform comprising the specimen. The light is reflected from the specimen through a reflective light path comprising an objective lens to the camera. The camera obtains an image of the specimen, and moves the specimen in an x, y, and z axis, continuing to take pictures until the entirety of the selected area is taken at high magnification. The acquired images are uploaded onto a server where they are viewed remotely for analysis. A remote user manipulates various views of the images and determines areas of interest for further analysis. The area of interest of the specimen is either collected for further analysis or subsequently imaged using the scanning system. The subsequent images are high resolution images of the area of interest of the specimen. These high resolution images provide important information on the mineral content of the specimen. The specimen may be collected or returned to the environment. The analysis of mineral content as well as coordinate information, are uploaded onto a database with corresponding image data. The data is stored by geolocation coordinate information so that it may be retrieved and displayed by any user using a geographic map.

Example 2

Image Analysis: Metallurgy (Mineral Analysis)

A metallurgical testing lab wants to provide to their clients a high magnification view of an entire specimen for reporting on failure analysis, metal fatigue, ferrite composition, coating analysis, grain size and grain flow, conditions after heat treating, material defects, spray coating coverage, porosity, and/or other indicators of the nature of a metallurgical sample. To this point, they have only been able to provide to their customers a single field of view, which could exclude important contextual data pertaining to the specimen, or multiple failure points. By embedding their samples in an epoxy resin and polishing them on an industrial polishing table, they are able to acquire multiple fields of view, reassembling them as a single continuous image which then can be remotely zoomed into and out of via a web interface, allowing their customers to analyze their samples in a detailed and thorough fashion.

Example 3

Field Study of the Grand Canyon

A team of California university researchers carry out a project of studying the geological formation of the Grand Canyon. The study is based on investigating rocks on the site of the Grand Canyon. However, the entire research team involves more than 10 people, and not all of them could go to the site together. The research team utilized the imaging apparatus disclosed in this application. The graduate students are sent out to the Grand Canyon for field study, while professors stayed in the university to conduct their daily teaching duties.

The graduate students travel to the south rim of the Grand Canyon. The imaging apparatus is connected in a motor home with a wireless network connected to the internet. Upon identifying rocks of interest, they use the imaging system to scan the rocks. The students are also able to scan rocks with a low resolution imaging setting, including rocks that are unknown to them. The low resolution images are then sent via a networking system to a server, optionally together with annotations taken by the graduate students. Furthermore, the students use their portable devices to take pictures, which coupled with a GPS system, allow the geolocation of the rocks to be recorded along with a photograph of the specimen, and sent to the server as well. By accessing the aforementioned data stored in the server, the professors can view the information (e.g., textures, colors, granularity, etc) of the rocks. Upon viewing the images, the professors are able to identify some rocks as useless and a few rocks as valuable. The professors further instruct the students to take detailed, high resolution images of the valuable rocks. The students again utilize the imaging apparatus to scan the high resolution images, which are sent to the server. The professors are able to evaluate the rocks based on the high resolution images.

The above research steps are repeated at various sites (e.g., west rim and north rim) throughout the Grand Canyon. The imaging apparatus automatically documents the locations of their rock studies, and further constructs a map of rocks found in the Grand Canyon. The maps enable the professors to real-time monitor/study the research findings. The virtual field trip that is assisted by the scanner dramatically increases the efficiency and effectiveness of the study.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of visualizing and analyzing a specimen in three-dimensions, wherein the specimen is an industrial, petrographic, geological, metallic or crystalline specimen, the method comprising the steps of:
   (a) placing a specimen on a substrate, the specimen occupying an area of the substrate;
   (b) placing the substrate on a stage and imaging the area of the substrate with the specimen using an objective lens of a microscope and crossed polarizer to obtain a single scan of the specimen at a first magnification and a first resolution, wherein the crossed polarizer is set in a single direction to provide data for an image of the specimen at a second resolution;
   (c) repeating the imaging process of step (b) with an angle of the crossed polarizer changed at various angled increments via synchronous rotation of an polarizer and an analyzer of the crossed polarizer, further comprising obtaining a continuous sequence of successive images by advancing a field of view of the objective lens of the microscope stepwise across the specimen and acquiring successive images of each field of view for the specimen, once at each angle of polarization; and
   (d) uploading and storing the image data at the second resolution in a database for remote viewing.

2. The method according to claim 1, further comprising obtaining images of the specimen at a third resolution, wherein the third resolution is lower than the second resolution.

3. The method according to claim 1, wherein the geological specimen is a crystalline specimen.

4. The method according to claim 3, wherein the geological specimen is a rock, mineral or crystal.

5. The method according to claim 1, wherein the specimen is a complete specimen.

6. A microscopy apparatus for visualizing and analyzing a specimen in three-dimensions, wherein the specimen is an industrial, petrographic, geological, metallic or crystalline specimen, comprising:
   (a) a device provided with at least one objective lens, a digital imaging system and a motorized stage;
   (b) a polarizer and an analyzer, the polarizer and analyzer forming a crossed polarizer, wherein the crossed polarizer is motorized and capable of rotating the polarizer and the analyzer synchronously, wherein the microscopy apparatus is controllable to obtain a single scan of the specimen at a first magnification and first resolution, and to provide digital image data of the specimen at a second resolution occupying an area of a substrate placed upon the motorized stage, the digital image data of the specimen comprising a continuous sequence of successive images by advancing a field of view of the objective lens stepwise across the specimen thereby acquiring successive images of the entire field of view for the specimen, and taking successive scans at different angle of polarization;
   (c) an image processing computer program to process the digital image data at the second resolution;
   (d) a storage medium to store digital image data obtained at the second resolution.

7. The apparatus according to claim 6, wherein the digital imaging system is a CCD camera, a CMOS or a line scanner.

8. The apparatus according to claim 6, wherein the specimen is a complete specimen.

9. The apparatus according to claim 6, wherein the specimen is a geological specimen.

10. The apparatus according to claim 9, wherein the geological specimen is a rock, mineral or crystal structure.

11. A method for acquiring image data for use in microscopy, the method comprising the steps of:
    (a) placing a substrate containing a prepared a geological specimen upon a stage of a microscope equipped with an objective lens, a digital imaging system and motorized stage, and a polarizer and an analyzer, the polarizer and analyzer forming a crossed polarizer capable of rotating synchronously, wherein the crossed polarizer is motorized;
    (b) imaging an area of the specimen using the objective lens to obtain a single scan of the specimen at a first magnification and a first resolution to provide digital image data of the specimen at a second resolution;
    (c) digitally processing the digital image data at the second resolution to obtain a copy of the image data at a third resolution lower than the second resolution, wherein the step of imaging comprises obtaining a continuous sequence of successive images by advancing a field of view of the objective lens of the microscope stepwise across the specimen and acquiring successive images of each field of view for the specimen, and taking multiple imaging passes at multiple angles of polarization;
    (d) transferring the copy of the image data at the third resolution from a data store to a remote digital processing device for displaying a corresponding lower resolution image, as a navigation map, upon a monitor of the digital processing device; and
    (e) optionally transferring corresponding image data at the second resolution of an area of the navigation map for the selected area of the image from the data store to an end-user.

12. The method according to claim 11, further comprising: storing the image data at the second resolution and the copy of the image data at the third resolution in a data store.

13. The method according to claim 12, further comprising processing the image data acquired for each image of each field of view, and storing the processed data in a data store.

14. The method according to claim 13, wherein the processing comprises one or more of digital image compression, and processing to remove peripheral shading around each image of each field of view.

15. The method according to claim 11, wherein during the imaging, the method further comprises periodically refocusing the microscope by moving the objective lens relative to the substrate.

16. A method of transferring digital image data comprising the steps of:
   (a) acquiring image data for a specimen using the method according to claim 11;
   (b) allowing access to the data store from a remote digital processing device;
   (c) transferring the data for the copy of the image data of the third resolution to the remote digital processing device;
   (d) displaying a corresponding image of the third resolution at the remote digital processing device; and
   (e) transferring corresponding image data of the second resolution of an area of the image with the third resolution for that area from the data store to the digital processing device.

17. The method according to claim 16, wherein transferring the corresponding image data of the second resolution at of an area of the image of the third resolution is achieved by selecting an area of the image at the third resolution displayed on a monitor of the digital processing device.

18. The method according to claim 16, further comprising the step of recording the areas of the image at the third resolution that are selected, for review of performance of a person performing the method.

* * * * *